(12) United States Patent  
Latour

(10) Patent No.: US 6,694,982 B2
(45) Date of Patent: Feb. 24, 2004

(54) GASTRIC BAND

(75) Inventor: Marie-Jeanne Latour, Bertrange (LU)

(73) Assignee: Surgical Diffusion SA, Saint Etienne (FR)

(*) Notice: Subject to any disclaimer, the term of this patent is extended or adjusted under 35 U.S.C. 154(b) by 0 days.

(21) Appl. No.: 10/098,059

(22) Filed: Mar. 14, 2002

(65) Prior Publication Data

US 2002/0169464 A1 Nov. 14, 2002

Related U.S. Application Data

(63) Continuation of application No. PCT/IB00/01293, filed on Sep. 13, 2000.

(51) Int. Cl.[7] ................................................ A61B 19/00
(52) U.S. Cl. .................... 128/869; 128/876; 606/157; 606/216
(58) Field of Search ................................. 606/148, 157, 606/216, 228; 128/899, 780, DIG. 26, 876; 24/16

(56) References Cited

U.S. PATENT DOCUMENTS

| | | | | |
|---|---|---|---|---|
| 3,648,703 A | * | 3/1972 | Manker | 128/DIG. 26 |
| 4,592,339 A | * | 6/1986 | Kuzmak | 128/346 |
| 4,696,288 A | | 9/1987 | Kuzmak et al. | 128/1 R |
| 5,074,868 A | * | 12/1991 | Kuzmak | 606/157 |
| 5,601,604 A | * | 2/1997 | Vincent | 606/216 |

FOREIGN PATENT DOCUMENTS

WO    WO 98/56321    12/1998

* cited by examiner

Primary Examiner—Michael A. Brown
(74) Attorney, Agent, or Firm—Heslin Rothenberg Farley & Mesiti P.C.

(57) ABSTRACT

The invention relates to a device for use in fitting around a stomach wall.

10 Claims, 4 Drawing Sheets

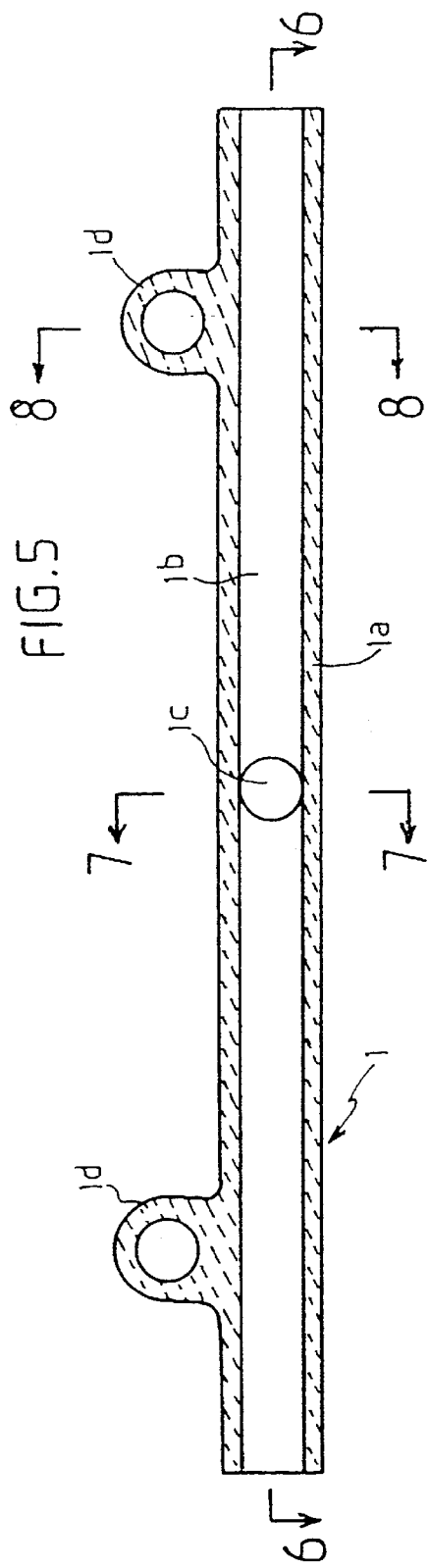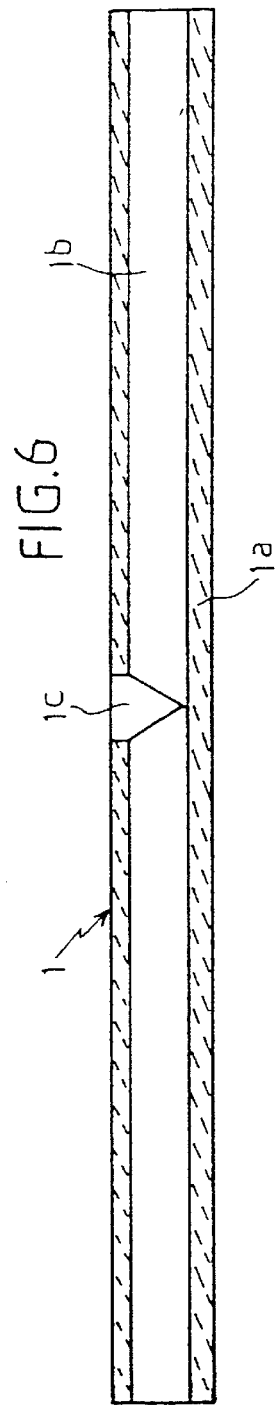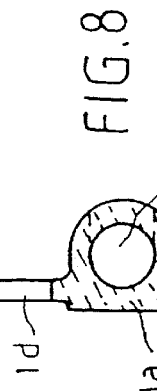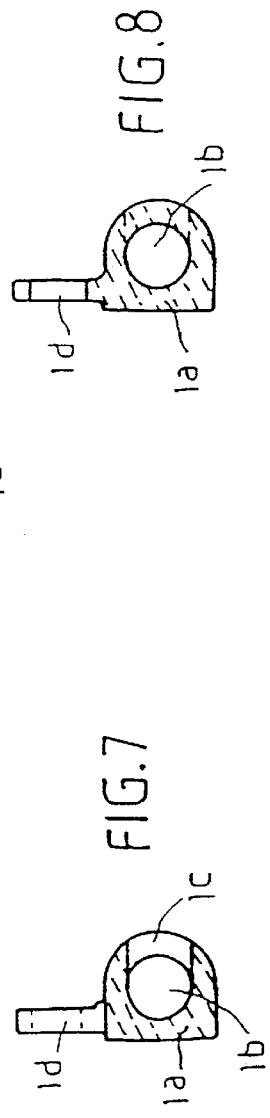

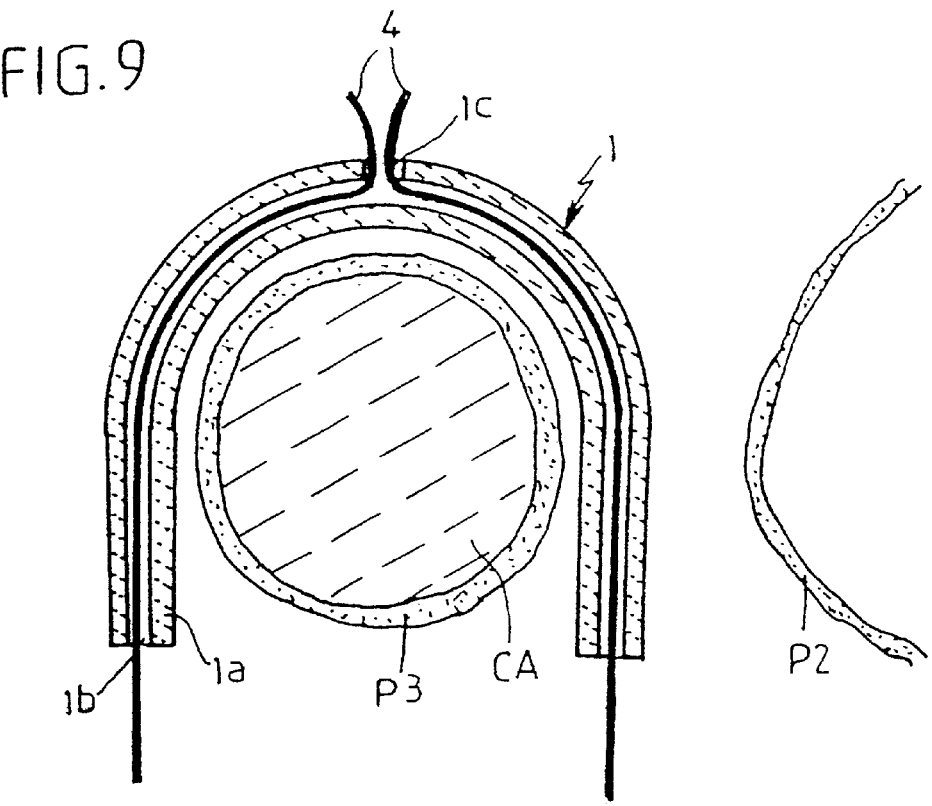
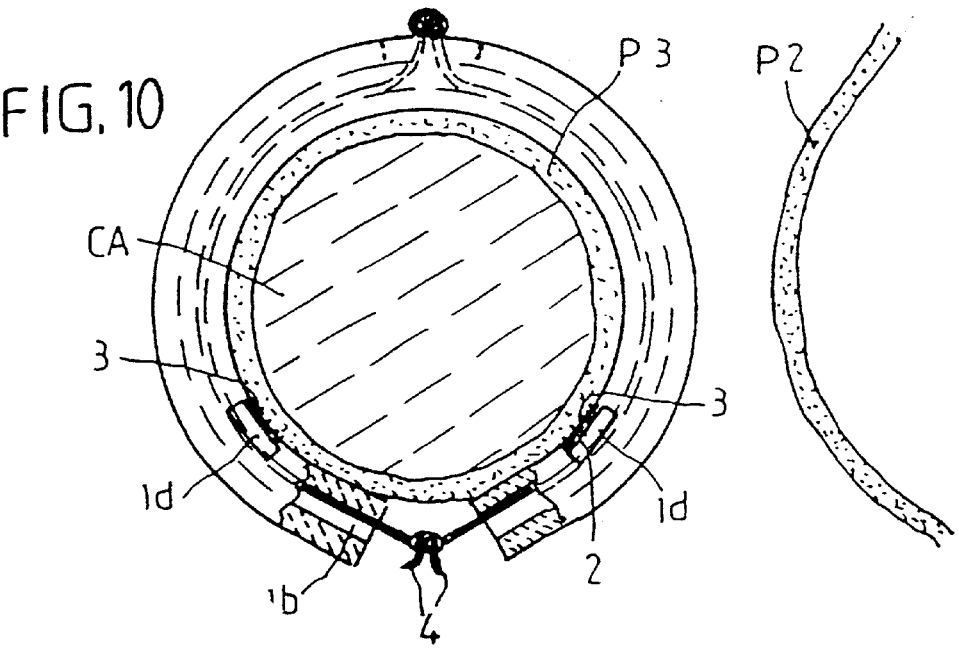

GASTRIC BAND

This application is a continuation of PCT application PCT/IB 00/01293 filed Sep. 13, 2000 designating the United States, and published in French as WO 01/19297 on Mar. 22, 2001. PCT/IB00/01293 claimed the priority of French application FR 99.11618 filed Sep. 14, 1999. The entire disclosures of all are incorporated herein by reference.

The invention relates to the technical sector of surgical apparatuses introduced into the human body to treat morbid obesity.

For many years surgical techniques have been developed to treat morbid obesity.

These techniques include introducing an intragastric balloon into the stomach which rapidly creates an impression of satiety during food intake, bypassing virtually all the intestine using an anastomosis between the jejunum and ileum, and the biliopancreatic bypass, but the techniques were rapidly abandoned as they proved ineffective over time and were the sources of many complications.

Efforts were then directed towards surgery for gastric restriction, i.e. creating a small cavity in the proximal section of the stomach which communicates with the rest of the stomach via a calibrated orifice. According to this technique, when the patient swallows food the small cavity quickly fills and creates an impression of satiety forcing the patient to eat slowly to enable the cavity to empty.

Various operation techniques have been implemented to achieve the above, particularly horizontal and vertical banded gastroplasty, i.e. creating a small cavity (P1) from the cardia (C) (the orifice between the stomach and the oesophagus), as shown in FIGS. 1 and 2, by separation then suture (S) and calibration of the orifice between small cavity (P1) and the rest of the stomach constituting the cavity (P2) by installing a band (A) made of biocompatible elastomer which is stapled to the stomach wall or simply positioned on the outside wall of the stomach, the inner diameter of which can be set by swelling.

This type of gastric band is described in U.S. Pat. No. 4,696,288 and German patent DE 19,751,733.

On the whole this technique is satisfactory and requires only a limited degree of invasiveness (using a coelioscopy or laparotomy). Nevertheless, the band occasionally twists around on itself or is moved through tilting and a new operation may be required which is both impractical and unpleasant for the patient concerned. Research has been carried out to improve this technique.

The gastric band of the invention overcomes these drawbacks by being perfectly positioned around the orifice separating the two cavities of the stomach, without the possibility of migration, and by being easily fitted.

In order to achieve the above and according to a first aspect, the band comprises fittings that enable the band to be firmly secured to said stomach wall via sutures after distortion of the band. The diameter of the passage between the two cavities thus defined is set using suture threads that are introduced into the band and tied at each end of said band after a calibrating apparatus has been introduced via the oesophagus. The longitudinal orifice of the tube formed in the body of the band communicates with a central orifice formed from the generating line opposite the flat edge in order to introduce the non-resorbable suture threads, the rear ends of which are tied or otherwise connected to the zone around said orifice and leave by the ends of the band in order to be tied to enable said band to be fastened into position.

These aspects and others will become apparent from the following description.

The object of the present invention is described, merely by way of example, in the accompanying drawings in which:

FIG. 5 is a longitudinal cross section through the band of the invention.

FIG. 6 is a top view and a cross section along line 6—6 of FIG. 5.

FIGS. 7 and 8 are transverse cross sections along lines 7—7 and 8—8 respectively of FIG. 5.

Figure 1:
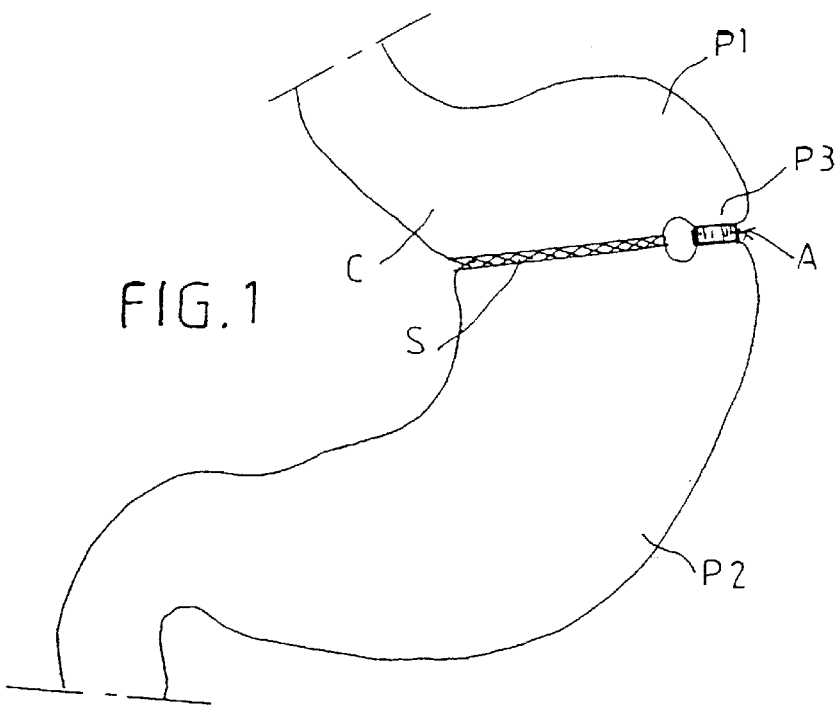
FIGS. 1 and 2 show a band installed for horizontal and vertical gastroplasty respectively according to the prior art.
Figure 2:
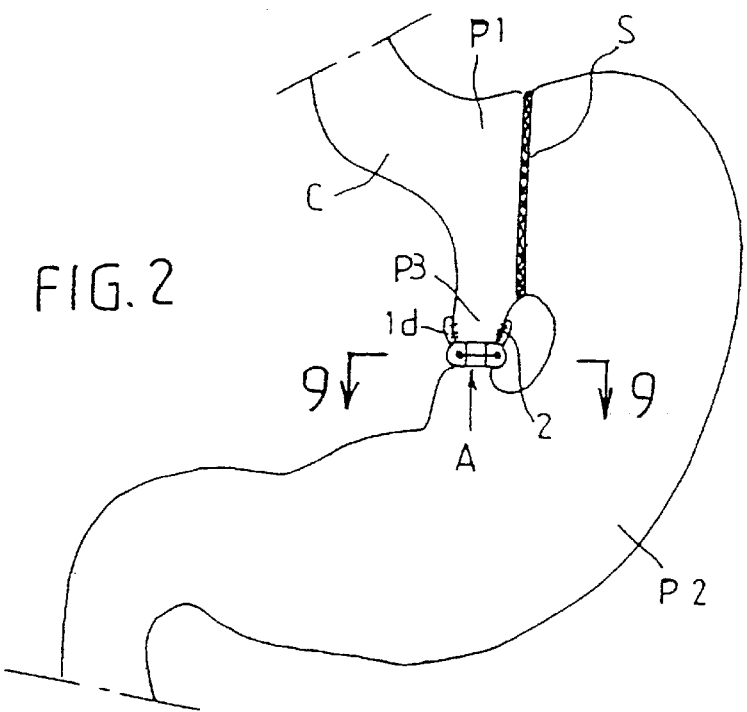
Figure 3:
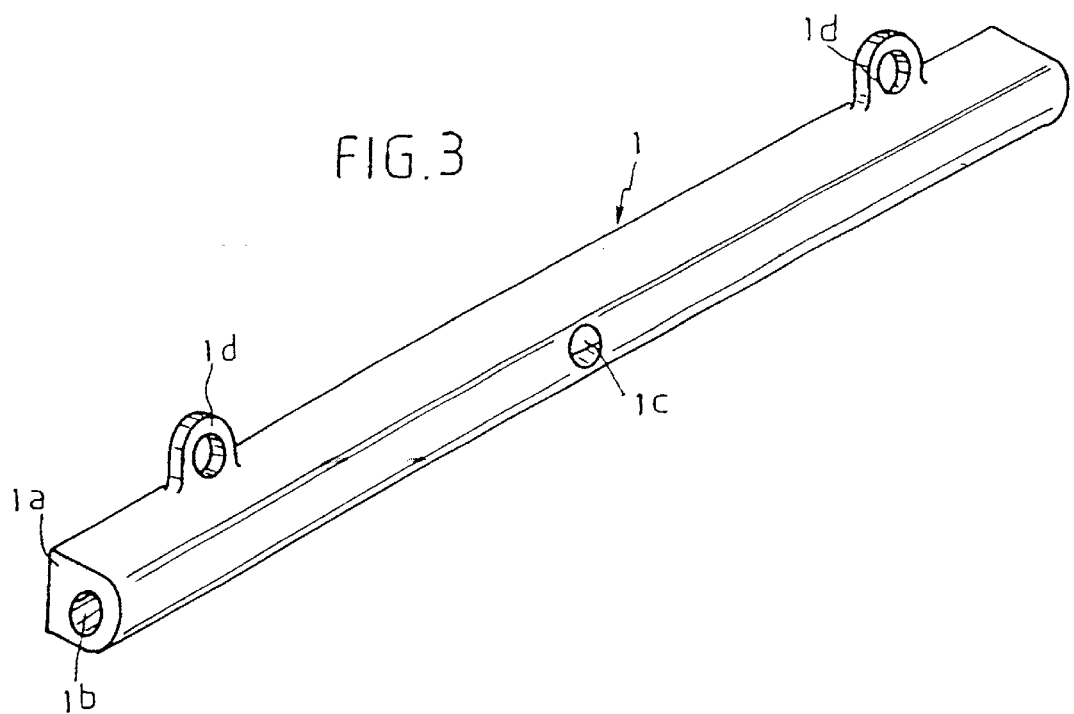
FIG. 3 is a perspective view of a band of the invention in the rest position.
Figure 4:
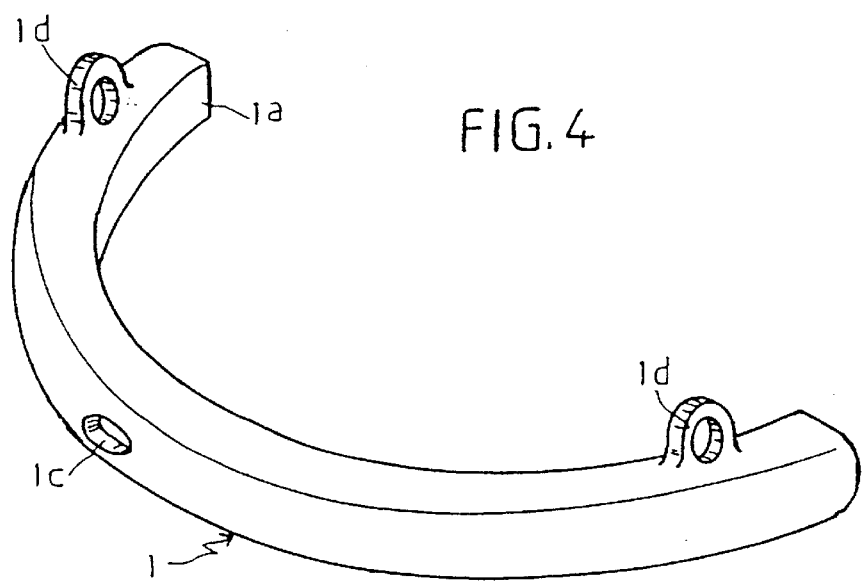
FIG. 4 is a perspective view of a band of the invention in the curved position.

FIG. 9 is a cross section along line 9—9 of FIG. 2 showing the fitting of the band of the invention in the section of the stomach to be restricted.

FIG. 10 is a partial cross section of FIG. 9 after the band has been set and tied.

In order that the present invention may more readily be understood, the following description is given, merely by way of example, reference being made to the accompanying figures.

As described in the preamble, a coelioscopy or laparotomy is performed to create a vertical partition by viscerosynthesis in the zone around the small gastric curve in the stomach either directly by applying a linear clip or after a circular transgastric anastomosis has been performed. The band of the invention is then fitted once it has been cleaned in a sterile solution.

The band (1) is made of a flexible, distortable and biocompatible material such as silicon elastomer as a tube with a generally circular cross section but the entire length of which (approximately 50 mm) has a flat edge (1a) that constitutes the bearing and contact surface with the stomach wall when the band is fitted around said wall.

The middle section of the longitudinal orifice (1b), which constitutes a channel in the body of the band, communicates with a central orifice (1c) formed from the generating line opposite the flat edge. Finally, near the ends of the tube there are at least two lugs or eyelets (1d) slightly set back from the flat edge and parallel to said flat edge.

As shown clearly in FIGS. 9 and 10, once the band has been fitted by being elastically distorted and curved around stomach wall (P3) separating the two cavities (P1, P2) mentioned above, which are constituted after anastomosis, and after a Faucher tube-type calibrating apparatus (CA) has been introduced via the oesophagus, the band is connected to stomach wall (P3) by suture stitches (2) using non-resorbable threads (3) attached to eyelets (1d). Then threads (4), which are also non-resorbable, are fed through central orifice (1c) and leave by both ends of the band via orifice (1b). The rear ends of the threads are then knotted at said central orifice then the band closes in on itself and is secured solidly to the wall by tension and knotting or gripping the ends that extend beyond the band, an operation controlled by the calibrating apparatus in order to achieve the required degree of shrinkage.

The advantages are made clear in the description. It should, however, be noted that the band is perfectly held in place by the lugs that are sutured to the stomach wall thereby preventing any tilting and by the flat edge which avoids any twisting or kinking. The non-invasive fitting technique means that it is possible to perform subsequent operations to modify or cancel the shrinkage without resulting in major complications.

The internal configuration of the band can be determined using any suitable shapes. The number of lugs can vary. The band is produced simply in that it is manufactured in straight strips that can be cut at regular intervals. The elastic distortion enables it to be suited to any type of stomach characteristics or individual. The flat-edge section prevents the band from sliding on the stomach wall and therefore makes the position stable.

What is claimed is:

1. Gastric band fitted around a stomach wall (P3) constituted by a vertical separation of the stomach on the side of the internal curve in the proximal section, then sutured in order to create a small cavity (P1) and a cavity (P2) with the rest of the stomach, the band (1) being made of an elastically distortable material as a tube the entire length of which has a flat edge (1a) intended to bear against the stomach wall (P3) to be restricted, characterized in that the band comprises fittings (1d) that enable the band to be firmly secured to said stomach wall via sutures (3) after distortion of the band, and in that the diameter of the passage between the two cavities thus defined is set using suture threads (4) that are introduced into the band and tied at each end of said band after a calibrating apparatus (CA) has been introduced via the oesophagus, and in that the longitudinal orifice (1b) extending through the length of of the band communicates with a central orifice (1c) formed the in a side of the band opposite the flat edge (1a), in order to introduce the non-resorbable suture threads (4) the rear ends of which are tied or otherwise connected to the zone around said orifice and leave by the ends of the band in order to be tied to enable said band to be fastened into position.

2. Band of claim 1, characterized in that the fittings that secure the band firmly to the restricted stomach wall (P3) consist of lugs or eyelets (1d) provided parallel to the flat edge (1a) and slightly set back from said flat edge, said lugs or eyelets being connected to said wall by non-resorbable suture threads (3).

3. Band of claim 1, characterized in that it the band is made of a silicon elastomer-type biocompatible material.

4. Band of claim 1, characterised in that the band is manufactured in straight strips that can be cut.

5. A device for use in fitting around a stomach wall wherein said device(1) comprises a gastric band(1) comprising elastic material, the entire length of which has a flat edge(1a) and wherein said flat edge adapted to bear against the stomach wall;

a longitudinal orifice(1b) through the entire length of said band;

a central orifice(1c) communicating with said longitudinal orifice, opening opposite said flat edge; and outwardly extending fittings(1d) attachable to the stomach wall via sutures(3) after distortion of said band.

6. The band of claim 5 wherein said fittings are lugs or eyelets and wherein said lugs or eyelets are parallel to said flat edge.

7. The band of claim 6 wherein said lugs or eyelets are offset from 0.1 mm to 1 mm from said flat edge.

8. The band of claim 5 wherein said elastic material comprises a biocompatible silicon elastomer.

9. The band of claim 5 wherein said central orifice is positioned within 20% of the longitudinal midpoint.

10. The band of claim 5 wherein said band is about 50 mm in length.

* * * * *

UNITED STATES PATENT AND TRADEMARK OFFICE
CERTIFICATE OF CORRECTION

PATENT NO.     : 6,694,982 B2
DATED          : February 24, 2004
INVENTOR(S)    : Latour It is certified that error appears in the above-identified patent and that said Letters Patent is hereby corrected as shown below:

<u>Column 3,</u>
Line 26, delete "formed the in a side" and insert -- formed in a side --

<u>Column 4,</u>
Line 5, delete the word "it" after the word "that"
Line 20, delete the word "wal1" and insert -- wall --

Signed and Sealed this

Eighteenth Day of May, 2004

JON W. DUDAS
*Acting Director of the United States Patent and Trademark Office*